(12) United States Patent
Cuesta et al.

(10) Patent No.: US 6,929,667 B2
(45) Date of Patent: Aug. 16, 2005

(54) METHOD FOR THE FLUORESCENT WHITENING OF COTTON

(75) Inventors: Fabienne Cuesta, Roppentzwiller (FR); Dieter Reinehr, Kandern (DE); Hans Kramer, Frick (CH); Georges Metzger, Moernach (FR); Bernd Wockenfuss, Lörrach (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/333,258

(22) PCT Filed: Jul. 12, 2001

(86) PCT No.: PCT/EP01/08062

§ 371 (c)(1),
(2), (4) Date: Apr. 14, 2003

(87) PCT Pub. No.: WO02/08511

PCT Pub. Date: Jan. 31, 2002

(65) Prior Publication Data

US 2003/0192137 A1 Oct. 16, 2003

(30) Foreign Application Priority Data

Jul. 20, 2000 (EP) .............................. 00810648

(51) Int. Cl.$^7$ .................. D06L 3/12; D06M 13/358; C07D 251/68
(52) U.S. Cl. ................ 8/648; 544/193.2; 8/442; 8/918
(58) Field of Search ............... 8/648, 442, 918; 544/193.2

(56) References Cited

U.S. PATENT DOCUMENTS

| 2,089,413 A | * | 8/1937 | Paine et al. ............... 106/164.3 |
| 3,475,190 A | * | 10/1969 | Fischer et al. .............. 252/582 |
| 5,493,022 A | | 2/1996 | Kaul et al. ................ 544/193.2 |

FOREIGN PATENT DOCUMENTS

| EP | 0708096 | | 4/1996 |
| EP | 0728749 | | 8/1996 |
| EP | 0850934 | | 7/1998 |
| FR | 905534 | * | 6/1944 |
| GB | 987922 | * | 3/1965 |
| GB | 1109537 | | 4/1968 |
| WO | 98/14435 | | 4/1998 |

* cited by examiner

Primary Examiner—Margaret Einsmann
(74) Attorney, Agent, or Firm—Kevin T. Mansfield

(57) ABSTRACT

A method for the fluorescent whitening of cotton in a discontinuous process comprising contacting the cotton, I an aqueous bath having a pH value of 6 or less, with one or more compounds of the Formula (I) wherein $R_1$ represents an $—SO_2R_3$, $—SOR_3$, $CO_2M$, $—CO_2R_3$, $—CONR_3R_4$, $—CN$ or $—NO_2$ substituent, $R_2$ is $—NH_2$, $—NH(C_1–C_4 \text{alkyl})$, $—N(C_1–C_4 \text{alkyl})_2$, $—NH(C_2–C_4 \text{hydroxyalkyl})$, $—N(C_2–C_4 \text{hydroxyalkyl})_2$, $—NH(C_1–C_4 \text{alkoxy})(C_1–C_4 \text{alkyl})$, $—N[(C_1–C_4 \text{alkoxy})(C_1–C_4 \text{alkyl})]_2$, $NHC_2–C_4 \text{alkylsulphonic acid}$, morpholineo, piperidino pyrrolidino, an amino acid or amino acid amide residue from which a hydrogen atom on the amino group has been removed, $—OC_1–C_4 \text{alkyl}$ or $—OC_1–C_4 \text{hydroxyalkyl}$, $R_3$ and $R_4$ each, independently, represent hydrogen, $C_1–C_4 \text{alkyl}$, $C_2–C_4 \text{hydroxyalkyl}$ or $C_1–C_4 \text{alkoxyC}_1–C_4 \text{alkyl}$ and M is H, Na, Li, K, Ca, Mg, ammonium, or ammonium that is mono-, di-, tri- or tetra-subsituted by $C_1–C_4 \text{alkyl}$, $C_2–C_4 \text{hydroxyalkyl}$ or a mixture thereof, some of which are new (1)

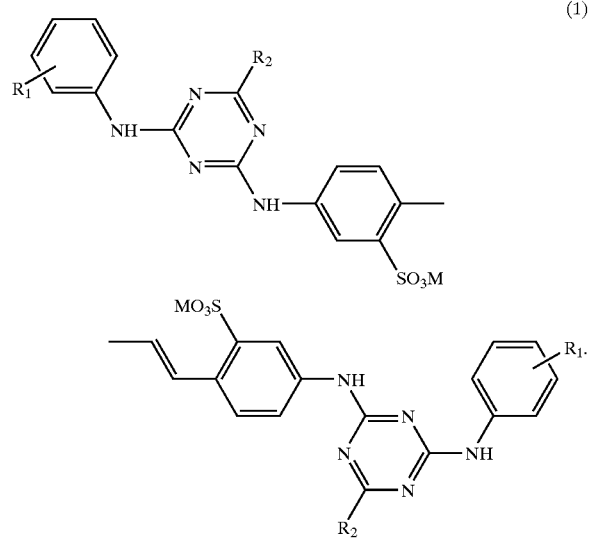

11 Claims, No Drawings

METHOD FOR THE FLUORESCENT WHITENING OF COTTON

The present invention relates to a method for the fluorescent whitening of cotton fabrics employing particular diaminostilbene fluorescent whitening agents having good acid stability and high affinity to cotton, some of which are new.

Fluorescent whitening agents (FWA's) are widely used in the textile industry in order to improve the whiteness properties of a large range of textile fibre materials. With particular reference to cotton, care must be taken in the choice of FWA and application technique, since FWA's exhibit a wide range of affinities.

In "batchwise" application methods, it is preferred to use FWA's which have a high affinity for cotton, since such FWA's exhibit a maximal exhaustion onto the cotton fibre from the bath.

For "continuous" processes, however, an FWA of low affinity must be used, namely one which provides the same whiteness effect at the start of the material as at the end, since it exhausts only onto a minor proportion of the material.

In the case of certain other applications, for example the "pad-batch" process, FWA's of intermediate affinity for cotton are required.

Moreover, FWA's are increasingly applied in discontinuous processes, in the course of which an acidic treatment, especially a finishing treatment using a polymer resin, occurs. In order to be effective in such processes, the FWA's used must exhibit a high fibre affinity. Unfortunately, however, most existing; high affinity FWA's are stable only in the pH range extending from alkaline to neutral values. Even at a pH value of only 6, most existing high affinity FWA's become turbid and form precipitates, with consequent reduction in their whitening effects. Moreover, in multistage processes, if such high affinity FWA's have already been applied in a first stage, when treated subsequently in an acid bath, they undergo a conversion which leads to green discolourations and to losses in whiteness levels.

To date, most high affinity FWA's have required a relatively low water solubility, which has led immediately to the formation of a precipitate, e.g. the free acid form of the FWA, at acidic pH values.

Certain novel FWA's which fulfill these criteria have been described in U.S. Pat. No. 5,656,760. However, for the preparation of these compounds, complex intermediates are required which must be prepared according to multi-step syntheses and, consequently, are disadvantageous both from a commercial and from an ecological point of view.

Surprisingly, it has now been found that certain, readily available FWA's, some of which are new, exhibit both a high affinity for cotton and an adequate stability in application baths having a pH value of 6 or below.

Accordingly, the present invention provides a method for the fluorescent whitening of cotton in a discontinuous process comprising contacting the cotton, in an aqueous bath bath having a pH value of 6 or less, with one or more compounds of the formula

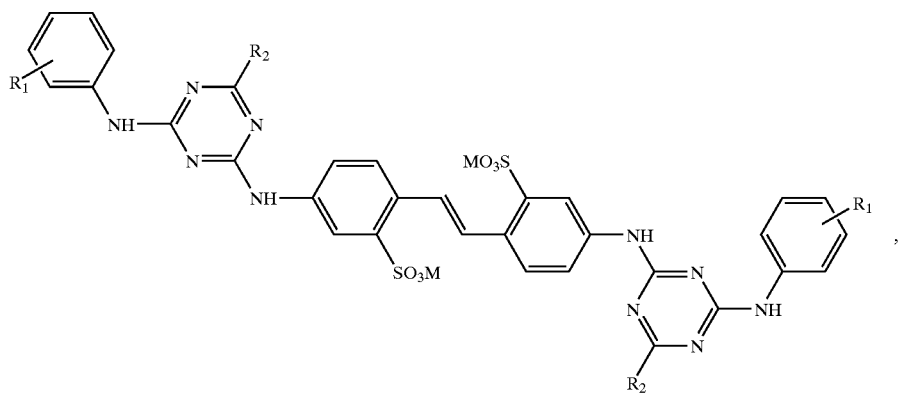

(1)

wherein
$R_1$ represents an —$SO_2R_3$, —$SOR_3$, —$CO_2M$, —$CO_2R_3$, —$CONR_3R_4$, —CN, or —$NO_2$ substituent,
$R_2$ is —$NH_2$, —$NH(C_1–C_4\text{alkyl})$, —$N(C_1–C_4\text{alkyl})_2$, —NH($C_2–C_4$hydroxyalkyl), —$N(C_2–C_4\text{hydroxyalkyl})_2$, —NH($C_1–C_4$alkoxy)($C_1–C_4$alkyl), —$N[(C_1–C_4\text{alkoxy})(C_1–C_4\text{alkyl})]_2$, $NHC_2–C_4$alkylsulphonic acid, morpholino, piperidino pyrrolidino, an amino acid or amino acid amide residue from which a hydrogen atom on the amino group has been removed, —$OC_1–C_4$alkyl or —$OC_1–C_4$hydroxyalkyl,
$R_3$ and $R_4$ each, independently, represent hydrogen, $C_1–C_4$alkyl, $C_2–C_4$hydroxyalkyl or $C_1–C_4$alkoxy$C_1–C_4$alkyl and
M is H, Na, Li, K, Ca, Mg, ammonium, or ammonium that is mono-, di-, tri- or tetrasubstituted by $C_1–C_4$alkyl, $C_2–C_4$hydroxyalkyl or a mixture thereof.

Preferably, the method employs a compound of formula (1) in which
$R_2$ is —$NH(C_1–C_4\text{alkyl})$, —$N(C_1–C_4\text{alkyl})_2$, —NH($C_2–C_4$hydroxyalkyl), —$N(C_2–C_4\text{hydroxyalkyl})_2$, morpholino, an amino acid or amino acid amide residue from which a hydrogen atom on the amino group has been removed, in particular from sarcosine, taurine, glutamic acid or aspartic acid or —$OC_1–C_4$hydroxyalkyl, especially hydroxyethoxy,
$R_3$ and $R_4$ each, independently, represent hydrogen, $C_1–C_4$alkyl or $C_2–C_4$hydroxyalkyl and
M is H, Na or K and, more preferably, a compound of formula (1) in which
$R_1$ represents an —$SO_2R_3$, —$CO_2M$ or —$CO_2R_3$ substituent situated in ortho- or para-position to the nitrogen atom,
$R_3$ and M being as previously defined.

As previously mentioned certain compounds of formula (1) are new. Consequently, a further aspect of the invention is a compound of the formula

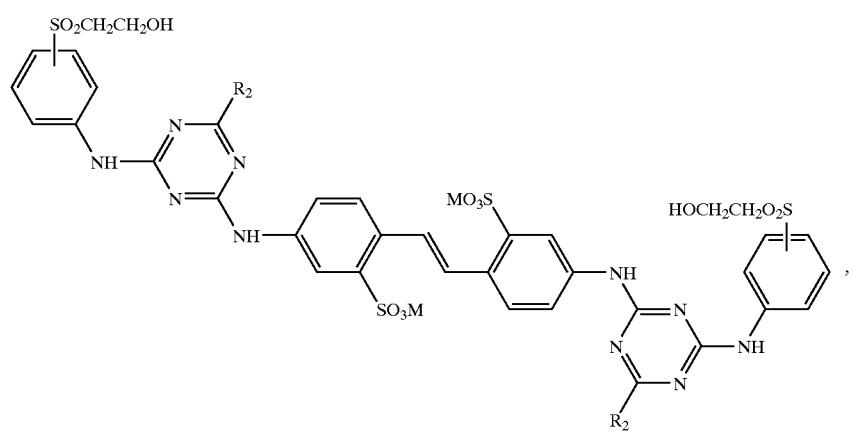

(2)

wherein
R$_2$ represents —NH(C$_2$–C$_4$hydroxyalkyl), —N(C$_2$–C$_4$hydroxyalkyl)$_2$ or an amino acid or amino acid amide residue from which a hydrogen atom on the amino group has been removed, and
M is as defined in claim 1.

Of particular interest is the compound of formula (2) in which the —SO$_2$CH$_2$CH$_2$OH group is in o- or p-position with respect to the anilino nitrogen atom,
R$_2$ represents —NH(C$_2$–C$_4$hydroxyalkyl), —N(C$_2$–C$_4$hydroxyalkyl)$_2$ or an amino acid residue derived from sarcosine, taurine, glutamic acid or aspartic acid and
M is H, Na or K and especially the compound of formula (2) in which,
R$_2$ is —N[CH$_2$CH(OH)CH$_3$]$_2$ or an aspartic acid residue and
M is Na.

When R$_2$, R$_3$, R$_4$ or M, in the definition of formulae (1) or (2), contains a C$_1$–C$_4$alkyl group, this may be, for example, a methyl, ethyl, n-propyl, isopropyl or an n-, s- or t-butyl group.

When R$_2$, R$_3$, R$_4$ or M, in the definition of formulae (1) or (2), contains a C$_2$–C$_4$hydroxyalkyl group, this may be, for example, hydroxyethyl, hydroxypropyl or hydroxybutyl.

When R$_2$, R$_3$, R$_4$ or M, in the definition of formulae (1) or (2), contains a (C$_1$–C$_4$alkoxy)(C$_1$–C$_4$alkyl) group, this may be, for example, a methyl, ethyl, n-propyl, isopropyl or an n-, s- or t-butyl group which is substitute by methoxy, ethoxy, propyloxy or butyloxy.

When R$_2$, in the definition of formulae (1) or (2), contains a C$_2$–C$_4$alkylsulphonic acid group, this may, for example be an ethyl, propyl or butyl sulphonic acid group.

The compounds of formula (2) may be produced by known methods, for example, by reacting cyanuric chloride, in any desired sequence, with the sodium salt of 4,4'-diaminostilbene-2,2'-disulphonic acid, a compound of the formula

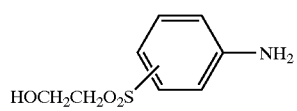

and a compound capable of introducing the group R$_2$ into the triazine ring.

The reactants are preferably used in substantially stoichiometric proportions required to form the compounds of formula (2).

As indicated above, the present invention provides a method for the fluorescent whitening of cotton in a discontinuous process comprising contacting the cotton, in an aqueous bath having a pH value of 6 or less, preferably one having a pH value of from 4 to 6, with one or more compounds having the formula (1).

Some of the compounds of formula (1) may be advantageously applied in dispersed form. For this purpose, they may be milled with an appropriate dispersant, conveniently using quartz balls and an impeller, down to a particle size of 1–2 microns.

As dispersing agents for such compounds there may be mentioned:
acid esters or their salts of alkylene oxide adducts, e.g., acid esters or their salts of a polyadduct of 4 to 40 moles of ethylene oxide with 1 mole of phenol, or phosphoric acid esters of the adduct of 6 to 30 moles of ethylene oxide with 1 mole of 4-nonylphenol, 1 mole if dinonyl phenol or, especially, with 1 mole of compounds which have been produced by the addition of 1 to 3 moles of styrene on to 1 mole of phenol;
polystyrene sulphonates;
fatty acid taurides;
alkylated diphenyloxide-mono- or -di-sulphonates;
sulphonates of polycarboxylic acid esters;
addition products of 1 to 60, preferably 2 to 30 moles of ethylene oxide and/or propylene oxide on to fatty amines, fatty amides, fatty acids or fatty alcohols, each having 8 to 22 carbon atoms, or on to tri- to hexavalent C$_3$–C$_6$alkanols, the addition products having been converted into an acid ester with an organic dicarboxylic acid or with an inorganic polybasic acid;
lignin sulphonates; and, in particular
formaldehyde condensation products, e.g., condensation products of lignin sulphonates and/or phenol and formaldehyde; condensation products of formaldehyde with aromatic sulphonic acids, e.g., condensation products of ditolylethersulphonates and formaldehyde; condensation products of naphthalenesulphonic acid and/or naphthol- or naphthylamine-sulphonic acids and formaldehyde; condensation products of phenolsulphonic acids and/or sulphonated dihydroxydiphenylsulphone and phenols or cresols with formaldehyde and/or urea; or condensation products of diphenyloxide-disulphonic acid derivatives with formaldehyde.

The compound of formula (1) may be used in the method of the present invention together with a minor proportion of one or more adjuvants. Examples of adjuvants include emulsifiers, perfumes, colouring dyes, opacifiers, bactericides, nonionic surfactants, anti-gelling agents such as nitrites or nitrates of alkali metal salts, especially sodium, nitrate, and corrosion inhibitors such as sodium silicate.

The amount of each of these optional adjuvants is preferably within the range of from 0.01 to 1% by weight of the aqueous treatment bath.

The method of the present invention is usually conducted in the temperature range of from 20 to 140° C., for example at or near to the boiling point of the aqueous bath, e.g. at about 90° C.

The method of the present invention is conveniently conducted using an exhaust or foulard technique.

The method of the present invention may be combined with a textile treatment or finishing method, for example, in the presence of a bleaching agent such as hydrogen peroxide.

It is often advantageous to use the compound of formula (1) in admixture with a minor amount of an assistant or extender such as anhydrous sodium sulphate, sodium sulphate decahydrate, sodium chloride, sodium carbonate, an alkali metal phosphate such as sodium or potassium orthophosphate, sodium or potassium pyrophosphate or sodium or potassium tripolyphosphate, or an alkali metal silicate such as sodium silicate.

The following Examples further illustrate the present invention.

PREPARATIVE EXAMPLES

Example 1a

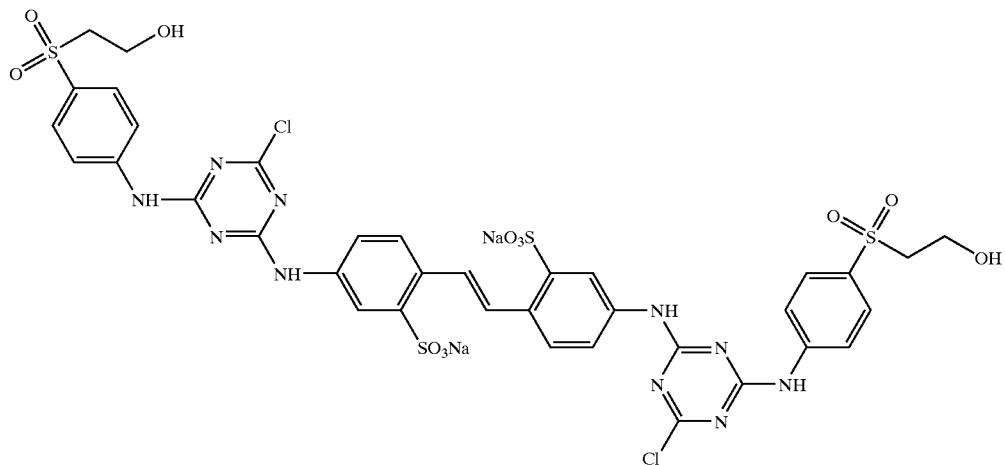

(101)

15 g of cyanuric chloride are dissolved in 175 ml, of acetone and the solution poured onto 175 g of ice/water. To the resulting suspension, a solution of 16.3 g of 4-(2-hydroxyethylsulphonyl)aniline in 50 ml of acetone is then added with stirring over 5 minutes. The pH is then adjusted to 6 by the addition of 40 ml of 1 M aqueous sodium carbonate solution and the mixture stirred for 1 hour, during which time the temperature rises to 25° C. The reaction mixture is filtered, the residue washed with acetone and then suspended in 200 ml of acetone and 90 g of ice/water. To this suspension is then added, with stirring, over 15 minutes, a solution of, 15.12 g of 4,4'diaminostilbene-2,2'-disulphonic acid in 120 ml of water, 71 g of ice/water and 40 ml of 2N aqueous sodium hydroxide solution. During the addition, the pH is maintained at between 7.0 and 7.5 by the addition of 40 ml of 1M aqueous sodium carbonate solution and the temperature rises to 50° C. After stirring for a further 3 hours, sodium chloride solution is added, the precipitate filtered off, washed with acetone and water and dried under vacuum at 80° C. to yield the compound of formula (101).

Elemental Analysis for $C_{36}H_{28}Cl_2N_{10}Na_2O_{12}S_4 \cdot 3.8H_2O \cdot 1.3CH_3OH$:

calculated C 36.3%, H 3.9%, N 11.7%, S 10.8%, Cl 5.9%;
found C 36.3%, H 4.0%, N 11.6%, S 10.9%, Cl 5.9%.

Example 1b

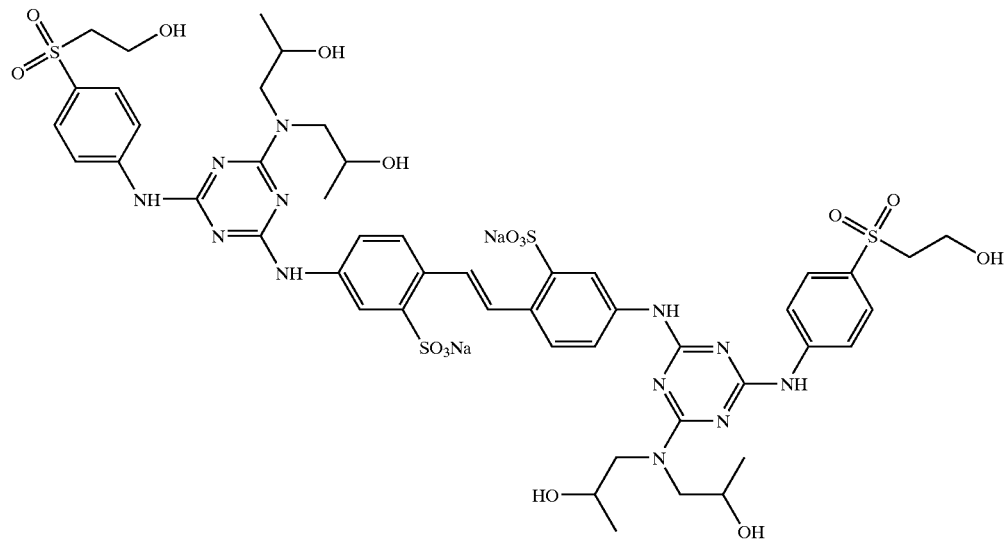

(102)

4.0 g of the compound (101) are stirred in 15 ml of water and 1.2 g of di-isopropanolamine are added. The mixture is then heated to 85° C., the pH being maintained at between 8.0 and 8.5 by the addition of 0.84 g of 32% aqueous sodium hydroxide solution. After stirring for 3 hours, the solution is cooled to room temperature and 20 ml of methanol are added. The resulting solution is then poured into 200 ml of isopropanol, the precipitated solids filtered and dried under vacuum at 80° C. to yield the compound of formula (102).

Elemental Analysis for $C_{48}H_{56}N_{12}Na_2O_{16}S_4 \cdot 8.4H_2O$:

calculated C 44.08%, H 5.30%, N 12.51%, S 9.54%, found C 44.05%, H 5.26%, N 12.53%, S 9.57%.

Example 2

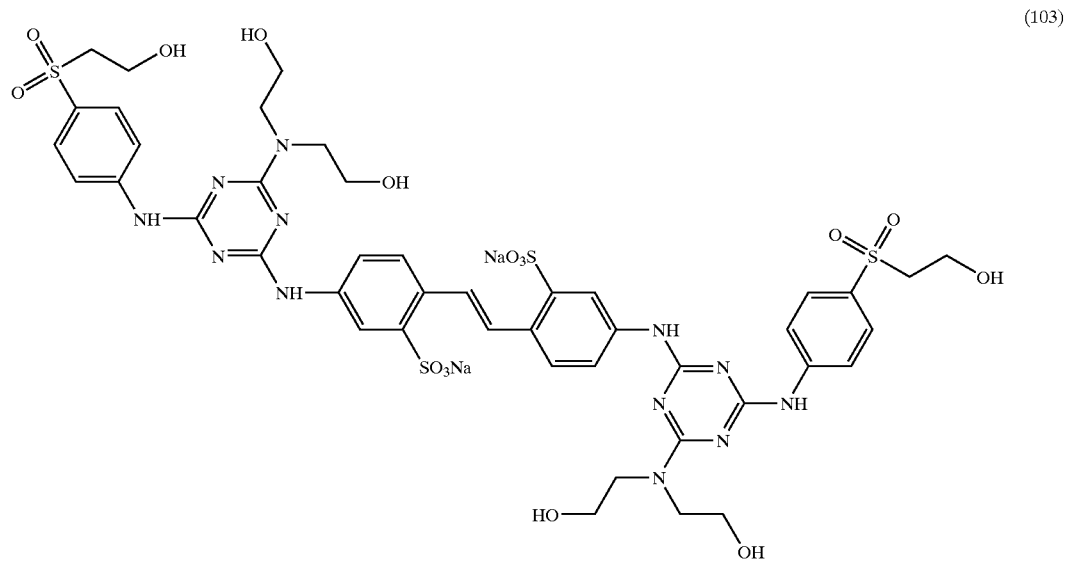

(103)

Proceeding as described in Example 1b, but replacing the di-isopropanolamine by 1.9 g of diethanolamine, the compound of formula (103) is obtained, having the following elemental analysis for $C_{44}H_{48}N_{12}Na_2O_{16}S_4 \cdot 1.5H_2O \cdot 1NaCl \cdot 1.7C_3H_8O$:

calculated C 43.20%, H 4.90%, N 12.30%, S 9.40%; found C 43.18%, H 4.90%, N 12.26%, S 9.43%.

Example 3

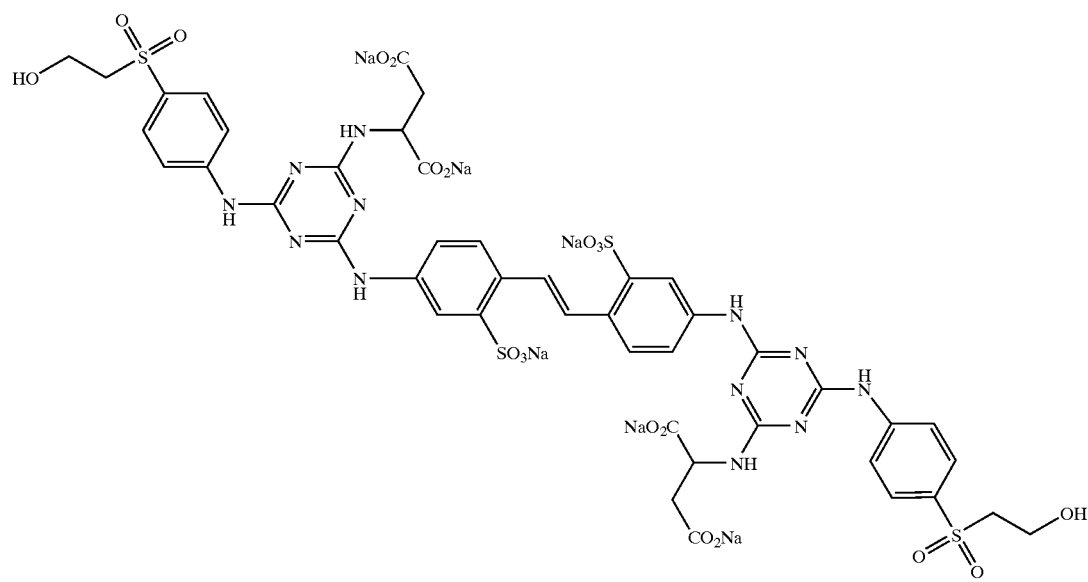

4.0 g of compound (101) are stirred in 10 ml of water. A solution of 1.0 g of aspartic acid in 10 ml of water containing 1.7 g of 32% aqueous sodium hydroxide solution is added to the suspension. The mixture is then heated to 90° C. and 10 ml of polyethylene glycol 300 are added, the pH being maintained at 8.0 by the addition of 0.84 g of 32% aqueous sodium hydroxide solution. After stirring for 6 hours, the mixture is cooled to room temperature and 20 ml of water are added. The resulting solution is poured into 100 ml of methanol and the precipitated solids filtered. This product is suspended in 30 ml of acetone, filtered and dried at room temperature, yielding the compound of formula (104).

Elemental Analysis for $C_{42}H_{38}N_{12}Na_6O_{20}S_4 \cdot 10H_2O$:

calculated C 34.40%, H 3.98%, N 10.60%, S 7.46%; found C 34.50%, H 4.06%, N 10.60%, S 7.43%.

Example 4a

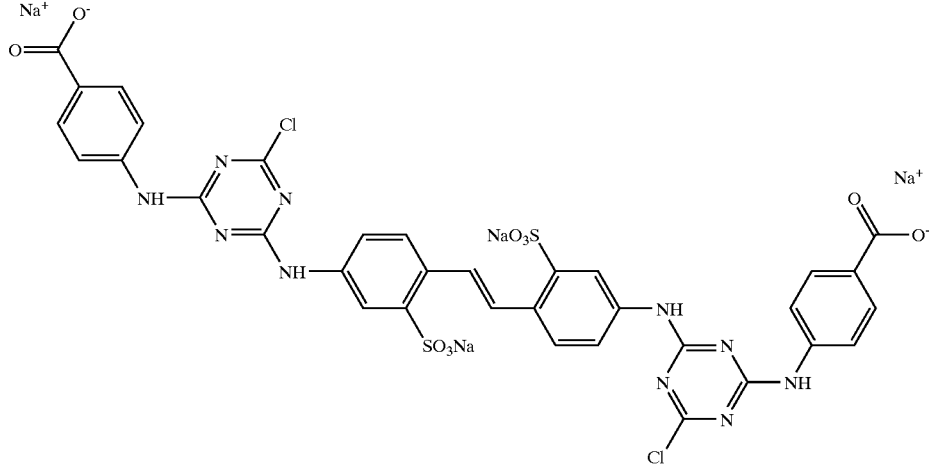

20 g of cyanuric chloride are dissolved in 128 ml of acetone and the solution poured onto 118 g of ice/water. To the resulting suspension, a solution of 24.8 g of 80.8% 4,4'diaminostilbene-2,2'-disulphonic acid in 210 ml of water and 94 g of ice/water is added with stirring over 25 minutes. After the addition, the pH is adjusted to and maintained at 4.5 during 40 minutes by the addition of 54 ml of a 1M aqueous sodium carbonate solution. A solution of 16 g of 4-aminobenzoic acid in 50 ml of water and 56 ml of a 1M aqueous sodium carbonate solution is then added. The pH is then adjusted to and maintained at 7.0–7.5 with 54 ml of a 1M aqueous sodium carbonate solution whilst stirring is continued for 1 hour, during which time the temperature rises to 40° C. After cooling, 200 ml of sodium chloride solution are added, the resulting precipitate filtered off, washed with water and dried under vacuum at 80° C. to yield the compound of formula (105).

Elemental Analysis for $C_{34}H_{20}Cl_2N_{10}Na_4O_{10}S_2.5.5H_2O.1.4NaCl$:

calculated C 36.00%, H 2.75%, Cl 6.23%, Cl⁻ 4.30%, N 12.30%, S 5.60%; found C 36.20%, H 2.97%, Cl 6.30%, Cl⁻ 4.50%, N 12.10%, S 5.66%.

Example 4b

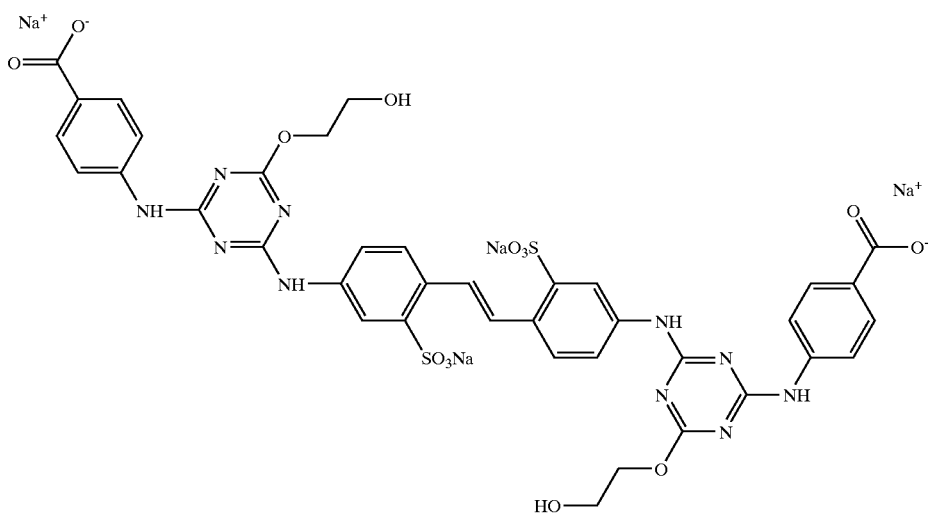

(106)

8 g of compound (105) are stirred in 110 ml, of ethylene glycol and 3 g of sodium carbonate are added. The mixture is heated to 130° C. and stirred at this temperature for 5 hours. After cooling, the reaction mixture is filtered, the filtrate poured into 700 ml of ethanol and stirred for 1 hour. The resulting precipitate is filtered off, washed with ethanol and dried under vacuum at 80° C. to yield the compound of formula (106).

Elemental Analysis for $C_{38}H_{30}N_{10}Na_4O_{14}S_2.4.25C_2H_6O$ (ethanol).1.4NaCl. 1.5Na$_2$CO$_3$:

calculated C 38.50%, H 4.15%, Cl⁻ 3.00%, N 9.40%, S 4.30%; found C 38.60%, H 4.18%, Cl⁻ 2.90%, N 9.35%, S 4.30%.

APPLICATION EXAMPLES

Example 5

Determination of Fibre Affinity

Various bleached cotton swatches are treated by the exhaust method in an aqueous bath having the following composition:

0.2% of test fluorescent whitener (100% active substance), based on the weight of the fibre,
0.5 ml/l Ultravon EL™,
20 ml/l 3% aqueous sodium hydroxide solutions,
2 ml/l 10% aqueous sodium silicate solution and
3 ml/l 35% aqueous hydrogen peroxide solution.

The fluorescent whiteners used were compounds (102)–(104) of the present invention and a commercial product having the formula

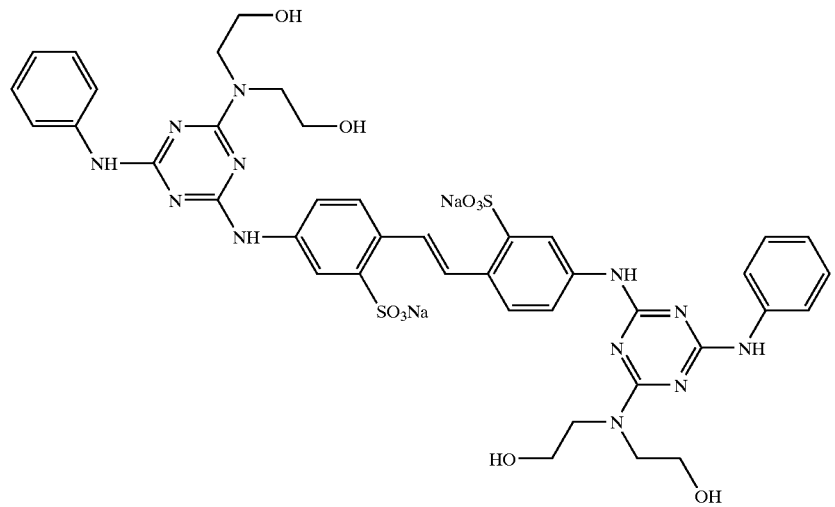

(100)

The treatment is conducted at a liquor ratio of 1:40 for 30 minutes at from 25 to 95° C., then for a further 60 minutes at 95° C. and, finally, cooled to 30° C. The swatches are removed from the treatment bath, rinsed and dried at 60° C.

Due to the high application temperature of 95° C., the tested compounds must have high affinity to cotton to provide high whiteness levels. Consequently, the whiteness values are a suitable measure of affinity, i.e. high whiteness corresponds to high affinity.

Whiteness was measured according to the method of Ganz, which is described in detail in the Ciba-Geigy Review, 1973/1 and also in the article "Whiteness Measurement", ISCC Conference on Fluorescence and the Colorimetry of Fluorescent Materials, Williamsburg, February 1972, published in the Journal of Color and Appearance, 1, No. 5 (1972).

The results of the measurements are shown in the following Table 1:

TABLE 1

| Compound No. | Whiteness Value |
|---|---|
| (102) | 234 |
| (103) | 224 |
| (104) | 150 |
| (100) | 237 |

The whiteness value of compounds (102) and (104) of the invention is only slightly lower than that of the conventional commercial FWA (103) and, consequently, both can be regarded as having high affinity to the fibre.

Example 6

Determination of pH Stability

The sensitivity of the test compounds (102)–(104) of the invention and of the commercial compound (103) to acidic pH values is evaluated in a bath and on the cotton fabric.

A solution containing 0.8 g/l of the test compound (as active ingredient) in drinking water (approximately 11° German hardness) is prepared and separate samples of the solution are adjusted to different pH values and stored in the dark at 25° C. The appearance of each sample is assessed immediately and also after 1, 2 and 4 hours storage.

Following the 4 hour appearance assessment, separate samples of bleached cotton are padded with the respective solutions (liquor pick-up 65%). The fabric samples are dried at 70° C. for 20 minutes and the whiteness values determined according to the method of Ganz.

The results of the observations are recorded in the following Table 2:

TABLE 2

| Compound No. | Time | pH 7 | pH 6 | pH 5 | pH 4 | pH 3 |
|---|---|---|---|---|---|---|
| (102) | Immediate | clear | clear | clear | clear | partly cloudy |
| (102) | 1 hour | clear | clear | clear | clear | partly cloudy |
| (102) | 2 hours | clear | clear | clear | clear | partly cloudy |
| (102) | 4 hours | clear | clear | clear | clear | partly cloudy |
| (102) | Whiteness | 193 | 193 | 194 | 192 | 171 |
| (103) | Immediate | clear | clear | clear | partly cloudy | cloudy |
| (103) | 1 hour | clear | clear | clear | cloudy | cloudy |
| (103) | 2 hours | clear | clear | clear | cloudy | cloudy |
| (103) | 4 hours | clear | clear | clear | cloudy | cloudy |
| (103) | Whiteness | 186 | 184 | 160 | 115 | 53 |
| (104) | Immediate | clear | clear | clear | clear | cloudy |
| (104) | 1 hour | clear | clear | clear | partly cloudy | cloudy |
| (104) | 2 hours | clear | clear | clear | partly cloudy | cloudy |
| (104) | 4 hours | clear | clear | clear | partly cloudy | cloudy |
| (104) | Whiteness | 195 | 196 | 193 | 189 | 55 |
| (100) | Immediate | clear | cloudy | cloudy | cloudy | cloudy |
| (100) | 1 hour | clear | cloudy | cloudy | cloudy | cloudy |
| (100) | 2 hours | clear | cloudy | cloudy | cloudy | cloudy |
| (100) | 4 hours | clear | cloudy | cloudy | cloudy | cloudy |
| (100) | Whiteness | 201 | 169 | 133 | 91 | 60 |

In contrast to the conventional high affinity FWA (100), which shows turbidity and serious loss of whiteness level, even at a pH value of 6, solutions containing the high affinity FWA's (102)–(104) of the invention can still be considered to be stable and show no significant loss of whiteness level even, in some cases, at a pH value as low as 4.

What is claimed is:

1. A method for the fluorescent whitening of cotton in a discontinuous process comprising contacting the cotton, in an aqueous bath having a pH value of 6 or less, with one or more compounds of the formula

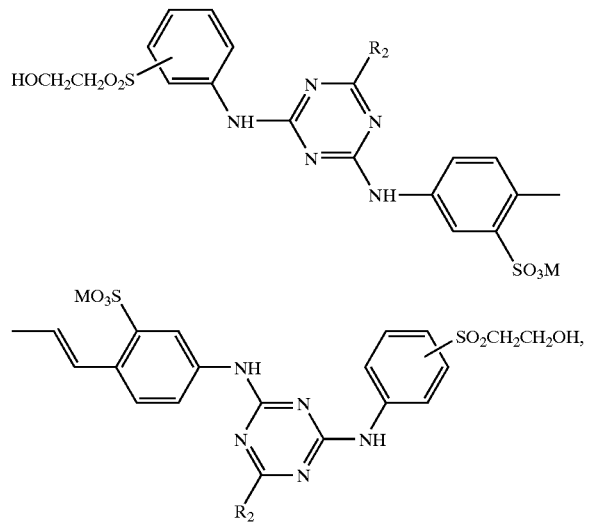

(2)

wherein $R_2$ is —$NH_2$, —$NH(C_1$–$C_4$alkyl), —$N(C_1$–$C_4$alkyl)$_2$, —$NH(C_2$–$C_4$hydroxyalkyl), —$N(C_2$–$C_4$hydroxyalkyl)$_2$, —$NH(C_1$–$C_4$alkoxy)($C_1$–$C_4$alkyl), —$N[(C_1$–$C_4$alkoxy)($C_1$–$C_4$alkyl)]$_2$, $NHC_2$–$C_4$alkylsulphonic acid, morpholino, piperidino pyrrolidino, an amino acid or amino acid amide residue from which a hydrogen atom on the amino group has been removed, —$OC_1$–$C_4$alkyl or —$OC_1$–$C_4$hydroxyalkyl, $R_3$ and $R_4$ each, independently, represent hydrogen, $C_1$–$C_4$alkyl, $C_2$–$C_4$hydroxyalkyl or $C_1$–$C_4$alkoxyC$_1$–$C_4$alkyl and M is H, Na, Li, K, Ca, Mg, ammonium, or ammonium that is mono-, di-, tri- or tetrasubstituted by $C_1$–$C_4$alkyl, $C_2$–$C_4$hydroxyalkyl or a mixture thereof.

2. A method according to claim 1 in which, in the compound of formula (2), $R_2$ is —$NH(C_1$–$C_4$alkyl), —$N(C_1$–$C_4$alkyl)$_2$, —$NH(C_2$–$C_4$hydroxyalkyl), —$N(C_2$–$C_4$hydroxyalkyl)$_2$, morpholino, an amino acid or amino acid amide residue from which a hydrogen atom on the amino group has been removed, or —$OC_1$–$C_4$hydroxyalkyl, $R_3$ and $R_4$ each, independently, represent hydrogen, $C_1$–$C_4$alkyl or $C_2$–$C_4$hydroxyalkyl and M is H, Na or K.

3. A method according to claim 1 in which the aqueous bath has a pH value in the range of from 4 to 6.

4. A method according to claim 1 in which the compound of formula (2) is used together with a minor proportion of one or more adjuvants selected from emulsifiers, perfumes, coloring dyes, opacifiers, bactericides, nonionic surfactants, anti-gelling agents and corrosion inhibitors.

5. A method according to claim 1 which is conducted in the temperature range of from 20 to 140° C.

6. A method according to claim 1 which is conducted using an exhaust or foulard technique.

7. A method according to claim 1 in which he compound of formula (2) is used in admixture with a minor amount of an assistant or extender.

8. A compound of the formula

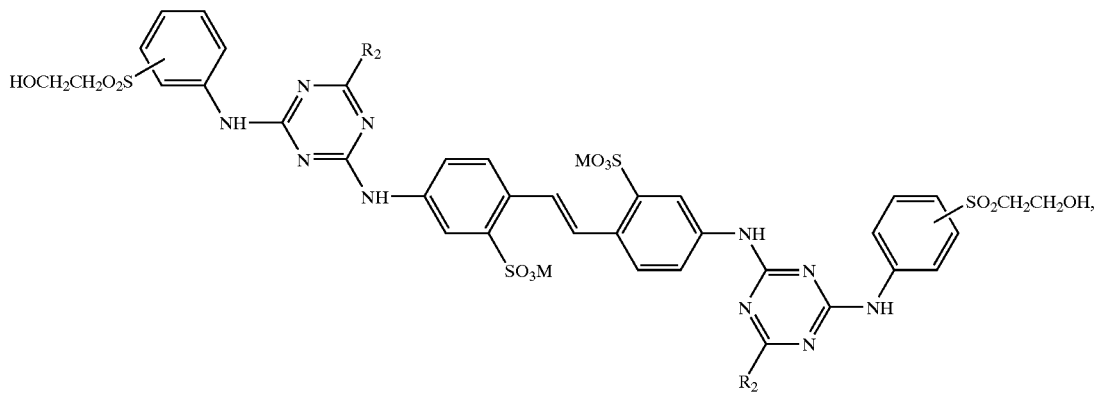

(2)

wherein $R_2$ represents —$NH(C_2$–$C_4$hydroxyalkyl), —$N(C_2$–$C_4$hydroxyalkyl)$_2$ or an amino acid or amino acid amide residue from which a hydrogen atom on the amino group has been removed, and M is H, Na, Li, K, Ca, Mg, ammonium, or ammonium that is mono-, di-, tri- or tetrasubstituted by $C_1$–$C_4$alkyl, $C_2$–$C_4$hydroxyalkyl or a mixture thereof.

9. A compound according to claim 8 in which the —$SO_2CH_2CH_2OH$ group is in o- or p-position with respect to the anilino nitrogen atom, $R_2$ represents —NH($C_2$-$C_4$hydroxyalkyl), —N($C_2$-$C_4$hydroxyalkyl)$_2$ or an amino acid residue derived from sarcosine, taurine, glutamic acid or aspartic acid and M is H, Na or K.

10. A compound according to claim 9 in which
$R_2$ is —N[CH$_2$CH(OH)CH$_3$]$_2$ or an aspartic acid residue and M is Na.

11. A method according to claim 2 in which, in the compound of formula (2), $R_2$ is an amino acid or amino acid amide residue of sarcosine, taurine, glutamic acid or aspartic acid from which a hydrogen atom on the amino group has been removed, or is hydroxyethoxy.

* * * * *